United States Patent [19]

Levitt et al.

[11] 4,453,970
[45] Jun. 12, 1984

[54] HERBICIDAL TRIAZINYL SULFONAMIDES

[75] Inventors: George Levitt; Chin-Lung Yeh, both of Wilmington, Del.; John C. Budzinski, West Chester, Pa.

[73] Assignee: E. I. Du Pont de Nemours and Company, Wilmington, Del.

[21] Appl. No.: 421,823

[22] Filed: Sep. 23, 1982

Related U.S. Application Data

[60] Division of Ser. No. 298,661, Sep. 3, 1981, Pat. No. 4,369,320, which is a continuation-in-part of Ser. No. 203,637, Nov. 3, 1980, abandoned.

[51] Int. Cl.³ .................. C07D 251/18; C07D 251/50; C07D 251/52; A01N 43/70
[52] U.S. Cl. .................................. 71/93; 544/212; 544/209; 544/207
[58] Field of Search ................ 544/212, 209, 207; 71/93

[56] References Cited

U.S. PATENT DOCUMENTS 4,127,405 11/1978 Levitt .................................. 544/211

Primary Examiner—John M. Ford

[57] ABSTRACT

N-[Heterocyclicaminocarbonyl]-8-quinolinesulfonamides such as N-[(4,6-dimethoxy-1,3,5-triazin-2-yl)aminocarbonyl]-8-quinolinesulfonamide or N-[(4,6-dimethoxypyrimidin-2-yl)aminocarbonyl]-8-quinolinesulfonamide are useful for plant growth retardation, brush control and weed control in crops.

29 Claims, No Drawings

HERBICIDAL TRIAZINYL SULFONAMIDES

RELATED APPLICATIONS

This is a division of application Ser. No. 298,661, filed Sept. 3, 1981 now U.S. Pat. No. 4,369,320, which in turn is a continuation-in-part of our copending application Ser. No. 203,637, filed Nov. 3, 1980, now abandoned.

BACKGROUND OF THE INVENTION

This invention relates to quinolinesulfonamides which are useful as agricultural chemicals.

French Pat. No. 1,468,747 discloses the following para-substituted phenylsulfonamides, useful as antidiabetic agents:

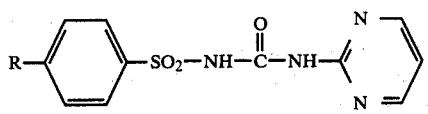

wherein R=H, halogen, $CF_3$ or alkyl.

Logemann et al. Chem. Ab., 53, 18052 g (1959), disclose a number of sulfonamides, including uracil derivatives and those having the formula:

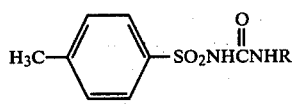

wherein R is butyl, phenyl or

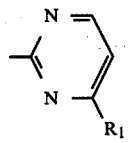

and $R_1$ is hydrogen or methyl. When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 125-5 (1962) [Chem. Ab., 59 1633 e] describes the synthesis of N-[(2,6-dimethoxypyrimidin-4-yl)aminocarbonyl]-4-methylbenzenesulfonamide:

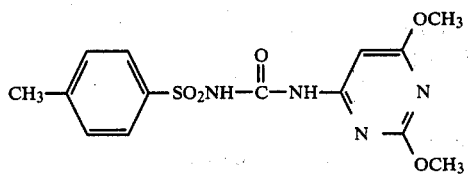

Based upon similarity to a known compound, the author predicted hypoglycemic activity for the foregoing compound.

Netherlands Pat. No. 121,788, published Sept. 15, 1966, teaches the preparation of compounds of Formula (i), and their use as general or selective herbicides,

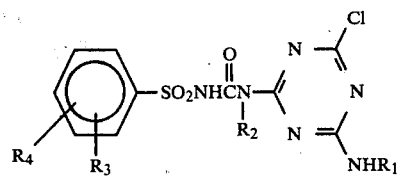

wherein $R_1$ and $R_2$ may independently be alkyl of 1–4 carbon atoms; and $R_3$ and $R_4$ may independently be hydrogen, chlorine or alkyl of 1–4 carbon atoms.

Compounds of Formula (ii), and their use as antidiabetic agents, are reported in J. Drug. Res. 6, 123 (1974).

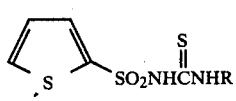

wherein R is pyridyl.

U.S. Pat. No. 3,689,549 (Sept. 5, 1972) to R. P. Williams discloses "heterocyclic sulfonamides wherein the heteroatoms are inert can also be used, e.g., compounds having the furan, thiophene or pyridine nucleus," in the production of sulfonyl isocyanates from sulfonamides in a sulfolane solvent.

B. G. Boggiano, V. Petrow, O. Stephenson and A. M. Wild, in *Journal of Pharmacy and Pharmacology* 13, 567-574 (1961) disclose the following compounds which were tested for hypoglycemic activity.

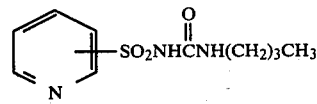

where

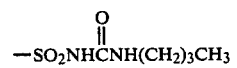

is in 2 or 3 position.

J. Delarge in *Acta Pol. Pharm.* 34, 245-249 (1977) discloses the following compounds as mild antiinflammatory agents. The 4-aryl-3-sulfonamides were disclosed as strong diuretics.

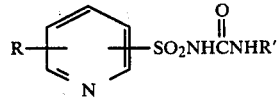

R=3-, 4-, 5-, 6-Me, 2-, 4-, 6-Cl, 3-Br, 4-$ET_2N$, 4-$Me_2CHNH$, 4-(3-$ClC_6H_4$)NH, 4-(3-$CF_3C_6H_4$)NH

R'=Et, Pr, $Me_2CH$, Bu

in 2, 3 and 4 position.

German Pat. No. 2,516,025 (Nov. 6, 1975) (to J. E. Delarge, C. L. Lapiere and A. H. Georges) discloses the following compounds as inflammation inhibitors and diuretics.

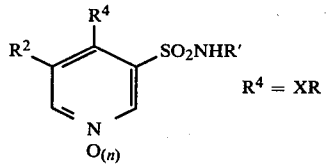

R=C$_6$H$_4$R$^3$(R$^3$=Cl, CF$_3$, Me, MeO, H, Br, F, NO$_2$, Et, NH$_2$), Et, iso-Pr, 4-methylfuryl, C$_6$H$_3$Cl$_2$-, C$_6$H$_3$(CF$_3$)Cl;
R'=alkylcarbamoyl, cyclohexylcarbamoyl, arylcarbamoyl, CSNHCH$_2$CH=CH$_2$, CONHC$_6$H$_4$Cl-p, alkylthiocarbamoyl, H, COEt;
R$^2$=H, Me;
X=NH, NMe, O, S, NEt; and
n=0,1.

U.S. Pat. No. 3,346,590 (Oct. 10, 1967) (to K. Dickere and E. Kühle) discloses the following pyridinesulfonyl isothiocyanates as novel compounds.

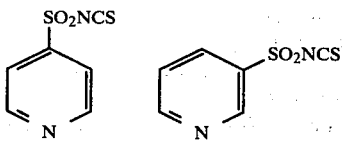

U.S. patent application Ser. No. 083,753 (now abandoned) discloses herbicidal pyridine sulfonylureas of Formula (iii).

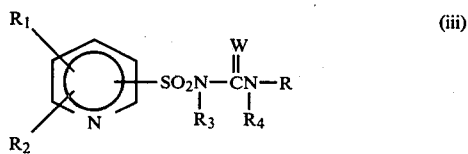

where R is

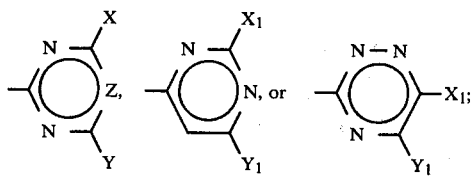

R$_3$ and R$_4$ are independently H or CH$_3$;
Z is CH or N; and
W is oxygen and sulfur.

U.S. patent application Ser. No. 033,752 discloses herbicidal isothioureas of Formula (iv).

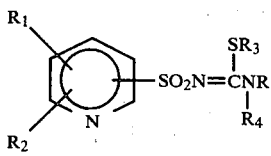

where R is

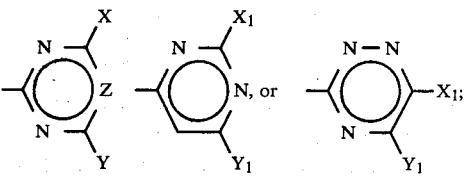

R$_3$ is C$_1$–C$_5$ alkyl; and
R$_4$ is H or CH$_3$.

The presence of undesired vegetation causes substantial damage to useful crops, especially agricultural products that satisfy man's basic food and fiber needs, such as cotton, rice, corn, wheat, soybean and the like. The current population explosion and concomitant world food and fiber shortage demand improvements in the efficiency of producing these crops. Preventing or minimizing the loss of a portion of such valuable crops by killing or inhibiting the growth of undesired vegetation is one way of improving this efficiency.

A wide variety of materials useful for killing or inhibiting (controlling) the growth of undesired vegetation is available; such materials are commonly referred to as herbicides. The need exists however, for still more effective herbicides that destroy or control weeds without cuasing significant damage to useful crops.

SUMMARY OF THE INVENTION

This invention relates to compounds of Formula I and their agriculturally suitable salts, suitable agricultural compositions containing them, and their method of use as preemergence and/or postemergence herbicides.

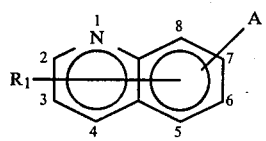

wherein
A is

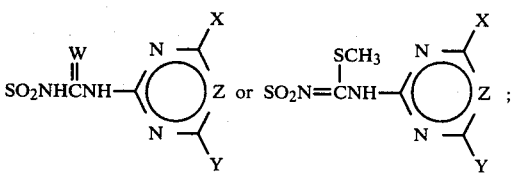

R$_1$ is H, F, Cl, Br, OCH$_3$, CH$_3$, NO$_2$, CO$_2$R$_2$, S(O)$_n$R$_3$, SO$_2$NR$_4$R$_5$, SO$_2$N(OCH$_3$)CH$_3$ or OSO$_2$R$_6$;
R$_2$ is C$_1$–C$_4$ alkyl, C$_3$–C$_4$ alkenyl, CH$_2$CH$_2$Cl or CH$_2$CH$_2$OCH$_3$;
R$_3$ is C$_1$–C$_4$ alkyl;
R$_4$ and R$_5$ are independently C$_1$–C$_4$ alkyl;
R$_6$ is C$_1$–C$_4$ alkyl or CF$_3$;
n is 0, 1 or 2;
X is C$_1$–C$_2$ alkyl, C$_1$–C$_2$ alkyl substituted with OCH$_3$, CF$_3$, C$_1$–C$_3$ alkoxy, N(CH$_3$)$_2$, NHCH$_3$, NH$_2$, or SCH$_3$;
Y is CH$_3$, OCH$_3$ or Cl;
Z is CH or N; and
W is O or S;

and their agricultural salts; provided that
(1) A is in the 5 or 8 position of the quinoline ring;
(2) when $R_1$ is $NO_2$, $CO_2R_2$, $S(O)_nR_3$, $SO_2NR_4R_5$, $SO_2N(OCH_3)CH_3$ or $OSO_2R_6$, then $R_1$ is at the 6-position when A is at the 5-position, and $R_1$ is at the 7-position when A is at the 8-position of the quinoline ring; $SO_2N(OCH_3)CH_3$ or $OSO_2R_6$, then $R_1$ is at the 6- or 7-position of the quinoline ring;
(3) the total number of carbon atoms of $R_4$ and $R_5$ is less than or equal to 5; and
(4) when Y is Cl, then Z is CH and X is $NH_2$, $NHCH_3$, $N(CH_3)_2$ or $OCH_3$.

Preferred for their higher herbicidal activity and/or more favorable ease of synthesis are:
(1) Compounds of the generic scope where A is in the 8-position of the quinoline ring; $R_1$ is H, Cl, Br, $OCH_3$, $CO_2CH_3$, or $NO_2$; and W is O.
(2) Compounds of Preferred (1) where $R_1$ is in the 7-position of the quinoline ring;
(3) Compounds of Preferred (2) where A is

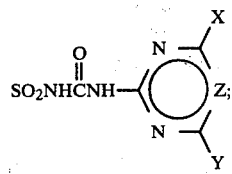

(4) Compounds of Preferred (3) where X is $CH_3$ or $OCH_3$; and
(5) Compounds of Preferred (4) where $R_1$ is H, Cl, Br or $OCH_3$.

Specifically preferred are:
N-[(4,6-dimethoxy-1,3,5-triazin-2-yl)aminocarbonyl]-8-quinolinesulfonamide, m.p. 151°-153°;
N-[(4,6-dimethoxypyrimidin-2-yl)aminocarbonyl]-8-quinolinesulfonamide, m.p. 175°-177°;
N-[(4,6-dimethylpyrimidin-2-yl)aminocarbonyl]-8-quinolinesulfonamide, m.p. 178°-185° (d);
N-[(4,6-dimethyl-1,3,5-triazin-2-yl)aminocarbonyl]-8-quinolinesulfonamide, m.p. 163°-173° (d);
N-[(4-methoxy-6-methylpyrimidin-2-yl)aminocarbonyl]-8-quinolinesulfonamide, m.p. 181°-183° (d);
N-[(4-methoxy-6-methyl-1,3,5-triazin-2-yl)aminocarbonyl]-8-quinolinesulfonamide, m.p. 151°-160° (d);
N-[(4-methoxy-6-methyl-1,3,5-triazin-2-yl)-N'-(8-quinolinylsulfonyl)carbamimidothioic acid, methyl ester, m.p. 205°-208°;
7-Chloro-N-[(4,6-dimethoxypyrimidin-2-yl)aminocarbonyl]-8-quinolinesulfonamide;
7-Chloro-N-[(4,6-dimethoxy-1,3,5-triazin-2-yl)aminocarbonyl]-8-quinolinesulfonamide;
7-Chloro-N-[(4,6-dimethylpyrimidin-2-yl)aminocarbonyl]-8-quinolinesulfonamide;
7-Chloro-N-[(4,6-dimethyl-1,3,5-triazin-2-yl)aminocarbonyl]-8-quinolinesulfonamide;
7-Chloro-N-[(4-methoxy-6-methylpyrimidin-2-yl)aminocarbonyl]-8-quinolinesulfonamide; and
7-Chloro-N-[(4-methoxy-6-methyl-1,3,5-triazin-2-yl)-aminocarbonyl]-8-quinolinesulfonamide.

This invention also relates to compounds of Formula V which are useful as novel herbicides as well as intermediates for the preparation of compounds of Formula I, where A is

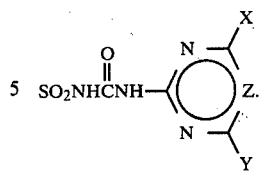

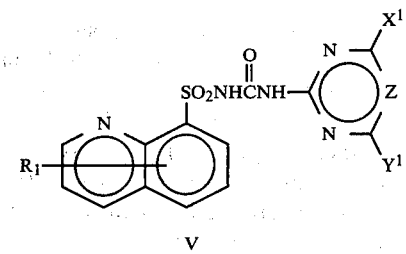

$R_1$ is H, F, Cl, Br, $OCH_3$, $CH_3$, $NO_2$, $CO_2R_2$, $S(O)_nR_3$, $SO_2NR_4R_5$, $SO_2N(OCH_3)CH_3$ or $OSO_2R_6$;
$R_2$ is $C_1$-$C_4$ alkyl, $C_3$-$C_4$ alkenyl, $CH_2CH_2Cl$ or $CH_2CH_2OCH_3$;
$R_3$ is $C_1$-$C_4$ alkyl;
$R_4$ and $R_5$ are independently $C_1$-$C_4$ alkyl;
$R_6$ is $C_1$-$C_4$ alkyl or $CF_3$;
n is 0 or 2;
$X^1$ and $Y^1$ are independently Cl or Br; and
Z is CH or N; provided that
(1) when $R_1$ is $NO_2$, $CO_2R_2$, $S(O)_nR_3$, $SO_2NR_4R_5$, $SO_2N(OCH_3)CH_3$ or $OSO_2R_6$, the $R_1$ is in the 7-position of the quinoline ring; and
(2) the total number of carbon atoms of $R_4$ and $R_5$ is less than or equal to 5.

Specifically preferred are:
N-[(4,6-dichloropyrimidin-2-yl)aminocarbonyl]-8-quinolinesulfonamide, m.p. 198°-200°; and
N-[(4,6-dichloro-1,3,5-triazin-2-yl)aminocarbonyl]-8-quinolinesulfonamide, m.p. 145°-147°.

Synthesis

The compounds of this invention can be made, as described in Schemes 1 through 8, from the appropriately substituted quinolinesulfonamides. These sulfonamides can be prepared by aminating, with aqueous ammonia, the corresponding sulfonyl chlorides by known methods e.g., Crossley et. al., J. Am. Chem. Soc. 60, 2222 (1938). Chlorosulfonation of appropriately substituted quinolines is known in the literature and affords the intermediate quinoline sulfonyl chlorides, e.g., J. Bankovskis, et. al., Latv. PSR Zinat. Akad. Vestis, Kim. Ser. 106 (1971). These procedures are outlined below in Scheme 1.

Scheme 1

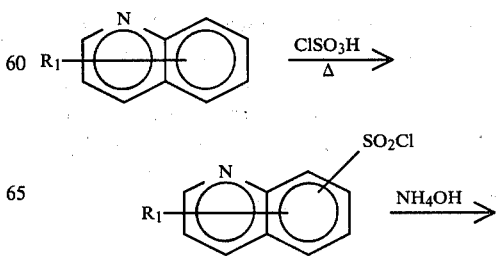

-continued

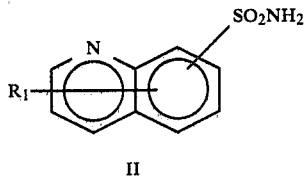

II

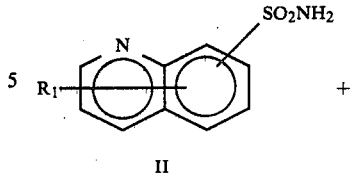

II +

In Scheme 2 below, compounds of structure (II), where $R_1 \neq SOR_3$, in dry tetrahydrofuran (THF) can be reacted with the heterocyclic isocyanate (III) where X', Y' and Z are as previously defined, to give (IV). Compounds of structure (IV) can be contacted with sodium methoxide in methanol at 25°–65° C. for 1–24 hours to give, after neutralization with acid such as HCl, compounds of structure (V).

Scheme 2

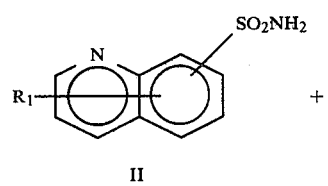

II +

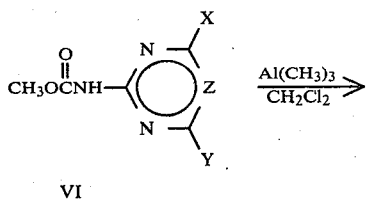

VI

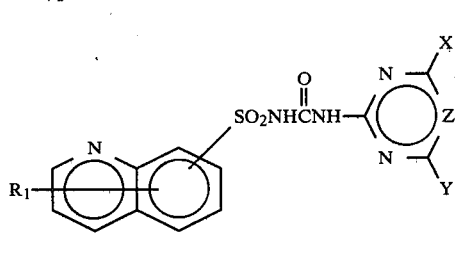

VII

The reaction of Scheme 3 is best carried out in methylene chloride at 25° to 40° C. for 24–96 hours under a nitrogen atmosphere. The product is isolated by the addition of an aqueous acetic acid solution and an aqueous hydrochloric acid solution followed by extraction of the product into methylene chloride or direct filtration of a product of low solubility. The product is purified by washing with solvents as methyl acetate, by trituration with solvents as n-butyl chloride or ether, or by column chromatography.

The required carbamates (VI) of Scheme 3 can be prepared by reacting the corresponding heterocyclic amines (VIII) with sodium hydride and dimethyl carbonate in an inert solvent at ambient temperature, as illustrated in Scheme 4 below. The synthesis of heterocyclic amine derivatives (VIII) has been reviewed in "The Chemistry of Heterocyclic Compounds", a series published by Interscience Publ., New York and London. 2-Aminopyrimidines are described by D. J. Brown in "The Pyrimidines", Vol. XVI of the above series. 2-Amino-1,3,5-triazines can be synthesized according to the methods described by E. M. Smolin and L. Rapaport in "s-Triazines and Derivatives," Vol. XIII of the same series.

Scheme 4

III

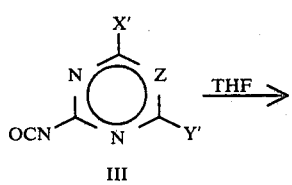

IV

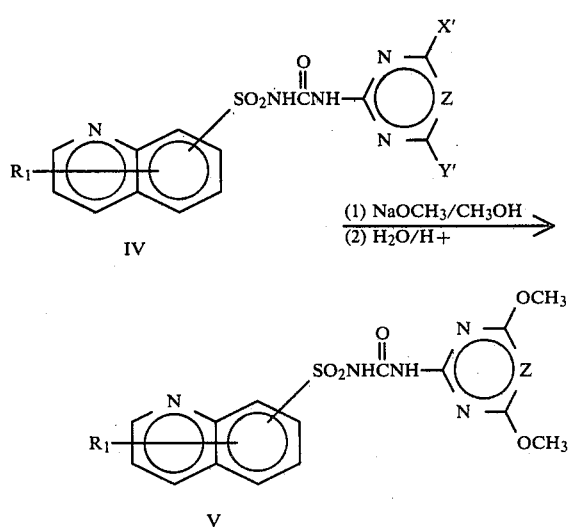

V

Compounds of Formula VII wherein $R_1 \neq CO_2R_2$ and $R_1 \neq SOR_3$ may be prepared by reacting the appropriately substituted quinolinesulfonamide (II) with the appropriate methyl pyrimidinyl carbamate or triazinyl carbamate (VI) in the presence of an equimolar or slight excess of trimethylaluminum according to the procedure of Scheme 3 below. $R_1$, X, Y and Z are as previously defined.

Scheme 3

VIII

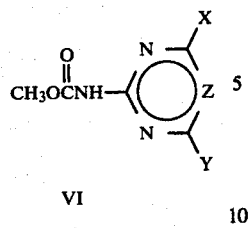

VI

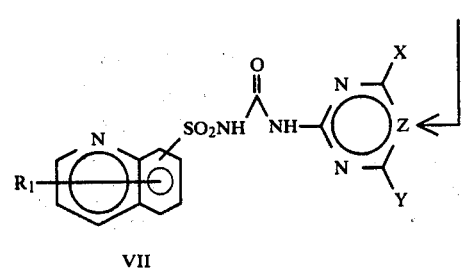

VII

In Scheme 5 below, compounds of structure (II) can be reacted with carbon disulfide and powdered potassium hydroxide at −5° to 25° in an inert polar solvent such as dimethylformamide (DMF) to form the corresponding dipotassium carbonimidodithioate. This compound can be dialkylated with excess alkyl halide and subsequently reacted at room temperature in an inert polar solvent such as DMF with a 2-aminoheterocycle to give compounds of structure IX.

Scheme 5

It should be noted that the method of choice for preparing a particular compound of structure (VII) is dependent upon the compatability of the $R_1$ group with the reaction conditions employed in the above schemes.

Compounds of structures (IX and X) can also be prepared as described in Scheme 7 below. Compounds of structure (II) can be reacted with a heterocyclic isothiocyanate by the method of Grantham and Levitt as described in unexamined European Patent 5986, herein incorporated by reference. This compound can be alkylated with methyl iodide and base in an inert solvent as described by Grantham and Levitt in unexamined European Patent No. 5986, herein incorporated by reference to give compounds of structure IX.

Scheme 7

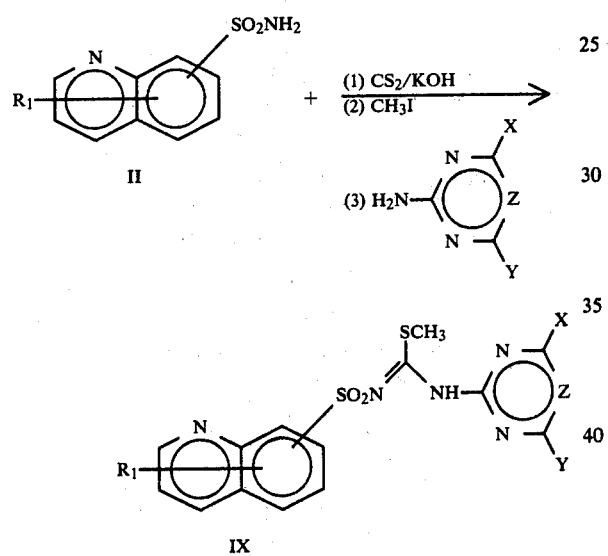

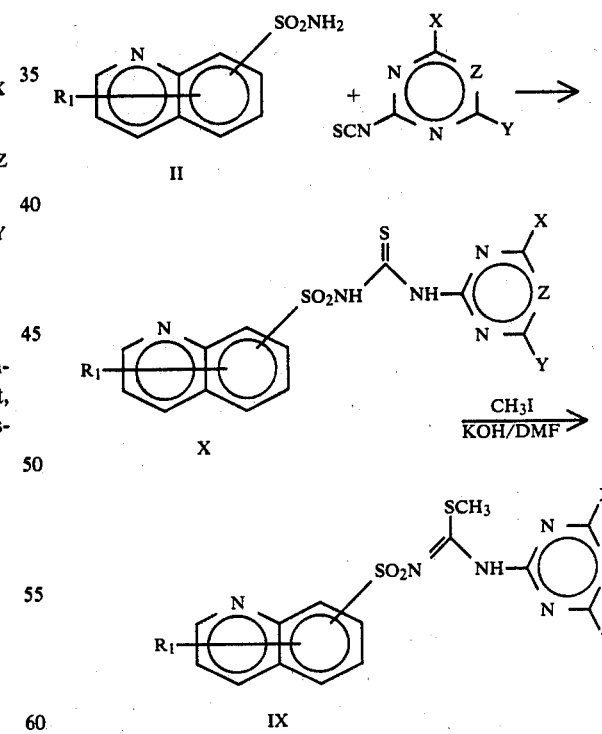

Compounds of structure IX can be converted to compounds of structure VII by methods taught in the art, e.g., unexamined European Pat. No. 0013480 as illustrated in Scheme 6 below.

Scheme 6

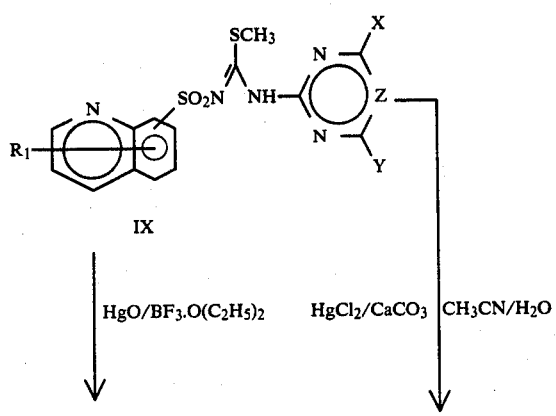

Compounds of Formula VIIb, where $R_1$ is $SOR_3$, can be prepared from the appropriate compounds of Formula VIIa, where $R_1$ is $SR_3$, by oxidation with m-chloroperbenzoic acid as shown in Scheme 8. X, Y and Z are as previously defined.

Scheme 8

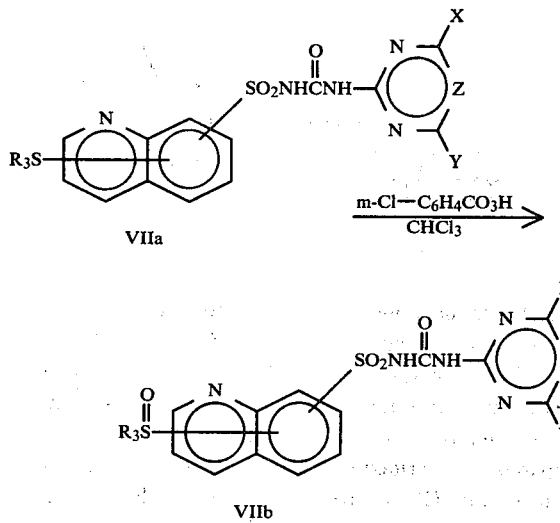

The compounds of this invention and their preparation are further illustrated by the following examples wherein temperatures are given in degrees centigrade and parts are by weight unless otherwise designated.

EXAMPLE 1

N-[(4,6-dichloro-1,3,5-triazin-2-yl)aminocarbonyl]-8-quinolinesulfonamide

To a stirred mixture of 2.12 g of 8-quinolinesulfonamide in 30 ml tetrahydrofuran is added 2.2 g of 2-isocyanato-4,6-dichloropyrimidine. The mixture is heated to reflux temperature for 2 hours, then cooled to room temperature and filtered to give 1.9 g white solid, m.p. 145°–147°. The infrared spectrum showed characteristic absorption bands at 3100–3500, 1715 cm$^{-1}$.

EXAMPLE 2

N-[(4,6-dichloropyrimidin-2-yl)aminocarbonyl]-8-quinolinesulfonamide

To a stirred mixture of 1.8 g of 8-quinolinesulfonamide in 15 ml tetrahydrofuran is added 2.3 g of 2-isocyanato-4,6-dichloro-1,3,5-triazine. This mixture is then heated to reflux temperature for 2½ hours, then cooled to room temperature, filtered and the resultant filtrate triturated with hexanes and filtered to give 1.8 g solid, m.p. 198°–200°.

EXAMPLE 3

N-[(4,6-dimethoxypyrimidin-2-yl)aminocarbonyl]-8-quinolinesulfonamide

To 0.86 g sodium methoxide in 15 ml methanol is added 1.6 g of N-[(4,6-dichloropyrimidin-2-yl)aminocarbonyl]-8-quinolinesulfonamide portionwise. This mixture is then heated to reflux temperature for 2 hours. The resultant white suspension is cooled to room temperature and filtered. The filtered white solid is dissolved up in a minimum amount of water and carefully acidified with 10% aqueous hydrochloric acid. The resultant white solid is filtered to give 0.65 g, m.p. 175°–177° C.

EXAMPLE 4

N-[(4,6-dimethoxy-1,3,5-triazin-2-yl)aminocarbonyl]-8-quinolinesulfonamide

To 1.9 g of N-[(4,6-dichloro-1,3,5-triazin-2-yl)-aminocarbonyl]-8-quinolinesulfonamide in 15 ml methanol is added 0.81 g of sodium methoxide (exotherm to 49° C.). The resultant thick suspension was stirred at room temperature for 1 hour. Water (~25 ml) is added and the mixture filtered. The aqueous phase is washed with ether and separated. The aqueous phase is cooled in an ice-water bath and acidified with concentrated hydrochloric acid. The resultant white suspension is filtered to give 0.5 g, m.p. 151°–153° C.

EXAMPLE 5

N-[(4-methoxy-6-methylpyrimidin-2-yl)aminocarbonyl]-8-quinolinesulfonamide

To a stirred mixture of 8-quinolinesulfonamide (4.2 g) in 100 ml methylene chloride is added a 2 M toluene solution of trimethylaluminum (15 ml). The resulting solution is stirred under N$_2$ for 45 min. Solid methyl (4-methoxy-6-methylpyrimidin-2-yl)carbamate (4.0 g) is added and the mixture is heated at reflux for 60 hrs. The reaction is quenched sequentially with acetic acid (2 ml) 6 N HCl (5 ml) and water (25 ml). The organic solution is retained, dried with MgSO$_4$, filtered, and is concentrated in vacuo to a crude solid. Washing with methyl acetate afforded 3.6 g of a pale yellow powder m.p. 181°–185° C. The infrared spectrum showed characteristic absorption bands at 3100 and 1700 cm$^{-1}$.

EXAMPLE 6

Methyl (4-methoxy-6-methylpyrimidin-2-yl)carbamate

2-Amino-4-methoxy-6-methylpyrimidine (50 g) was added portion wise to 50% sodium hydride (42.8 g) in 1 L dry THF. After stirring for ½ hour, dimethyl carbonate (58.5 g) was added dropwise with cooling. The mixture was stirred under nitrogen for ~16 hours at ambient temperature. Concentrated HCl (80 ml) was added slowly and using external cooling a pot temperature of ~25° C. was maintained. Saturated aqueous NaCl (80 ml) was then added. The solvents were decanted from the precipitated solids and dried over Na$_2$SO$_4$. Filtering and evaporating the solvents afforded the crude material which was recrystallized from hexane. 54 g m.p. 89°–92.5° C. The infrared spectrum showed characteristic absorption bonds at 3400 and 1760 cm$^{-1}$.

EXAMPLE 7

7-Chloro-N-[(4,6-dimethoxy-1,3,5-triazin-2-yl)aminocarbonyl]-8-quinolinesulfonamide To a stirred mixture of 7-chloro-8-quinolinesulfonamide (1.5 g) in 75 ml methylene chloride is added a 2 M toluene solution of trimethyl aluminum (4.7 ml). The resulting solution is stirred under N$_2$ for 45 min. Solid methyl(4,6-dimethoxy-1,3,5-triazin-2-yl)carbamate (1.1 g) is added and the mixture is heated at reflux for 60 h. The reaction is quenched sequentially with acetic acid (1 ml), 6 N HCl (2.5 ml) and water (13 ml). The organic solution is retained, dried with MgSO$_4$, and is concentrated to an oil-solid mixture. Filtration afforded 0.6 g yellow solid m.p. 169°–191° C. (dec). The infrared spectrum showed characteristic absorption bands at 3300 and 1700 cm$^{-1}$.

EXAMPLE 8

Carbonimidodithioic acid,
N-(8-quinolinylsulfonyl)-dipotassium salt

To a mixture of 20.8 g of quinoline-8-sulfonamide in 150 ml dimethylformamide was added 6.6 g of powdered potassium hydroxide. After 0.5 hour, the mixture had turned to a thick white slurry and 3.0 ml of carbon disulfide was added dropwise at room temperature. The mixture was stirred for 0.5 hour and 3.3 g of powdered potassium hydroxide and 1.5 ml of carbon disulfide was added. The mixture was then stirred 0.5 hour and 3.5 g of powdered potassium hydroxide and 2.0 ml carbon disulfide added. The mixture was then stirred for 1.5 hour at room temperature and poured into 1 liter of ethyl acetate. The resulting solid was collected, washed with ethyl acetate, then with diethyl ether and dried under vacuum to give 24 g of the desired product (m.p. 270°–290° with decomposition).

EXAMPLE 9

Carbonimidodithioic acid,
N-(8-quinolinylsulfonyl)-dimethyl ester

A mixture of 10.8 g of carbonimidodithioic acid, N-(8-quinolinylsulfonyl)dipotassium salt and 9.0 g methyl iodide in 100 ml methanol was stirred at room temperature overnight. The solid was filtered and washed with methanol to give 5.0 g of the above product.

NMR (DMSOd$_6$): δ3.3 (6H, s) (SCH$_3$); and δ7.5–9.1 (6H, m) (aryl).

EXAMPLE 10

Carbamimidothioic acid,
N-[4-methoxy-6-methyl-1,3,5-triazin-2-yl]-N'-[8-quinolinylsulfonyl]-, methyl ester To a suspension of 0.6 g of sodium hydride (48% dispersion) in 25 ml dimethylformamide was added 1.45 g of 2-amino-4-methyl-6-methoxy-1,3,5-triazine. The mixture was stirred under N$_2$ for 2 hours at room temperature then 3.0 g of carbonimidodithioic acid, N-(8-quinolinylsulfonyl)dimethyl ester was added portionwise. The mixture was then stirred for 2 hours at room temperature, filtered and poured into 250 g of ice-water. The solution was filtered to remove (0.3 g) of solid.

The filtrate was then acidified to a pH 4–6 with aqueous hydrochloric acid. The resulting solid was collected and dried under vacuum overnight to give 0.85 g of greenish solid, m.p. 205°–208°.

NMR (CF$_3$CO$_2$H): δ2.35 (3H, s)(CH$_3$); δ2.80 (3H, s)(S-CH$_3$); δ4.28 (3H, s)(OCH$_3$); and δ8.1–9.5 (6H, mult)(quinoline).

Using the procedures outlined previously and further illustrated by Examples 1 through 10, the compounds of Tables I through V may be prepared.

TABLE I

| R$_1$ | X | Y | Z | W | m.p. (°C.) |
|---|---|---|---|---|---|
| H | CH$_3$ | OCH$_3$ | CH | O | 181–185(d) |
| H | CH$_2$CH$_3$ | OCH$_3$ | CH | O | |
| H | CH$_2$OCH$_3$ | OCH$_3$ | CH | O | |
| H | CH$_2$CH$_2$OCH$_3$ | OCH$_3$ | CH | O | |
| H | OCH$_3$ | OCH$_3$ | CH | O | 175–177 |
| H | OCH(CH$_3$)$_2$ | OCH$_3$ | CH | O | |
| H | N(CH$_3$)$_2$ | OCH$_3$ | CH | O | |
| H | NH$_2$ | OCH$_3$ | CH | O | |
| H | SCH$_3$ | OCH$_3$ | CH | O | |
| H | CH$_3$ | CH$_3$ | CH | O | 178–185(d) |
| H | CF$_3$ | CH$_3$ | CH | O | |
| H | NH$_2$ | Cl | CH | O | |
| H | NHCH$_3$ | Cl | CH | O | |
| H | N(CH$_3$) | Cl | CH | O | |
| H | OCH$_3$ | Cl | CH | O | |
| H | CH$_3$ | OCH$_3$ | N | O | 151–150(d) |
| H | CH$_2$OCH$_3$ | OCH$_3$ | N | O | |
| H | OCH$_3$ | OCH$_3$ | N | O | 151–153 |
| H | OCH$_2$CH$_2$CH$_3$ | OCH$_3$ | N | O | |
| H | CH$_3$ | CH$_3$ | N | O | 178–185(d) |
| H | CH$_2$CH$_3$ | CH$_3$ | N | O | |
| 2-Cl | OCH$_3$ | OCH$_3$ | CH | O | |
| 2-Cl | CH$_3$ | OCH$_3$ | CH | O | |
| 2-Cl | CH$_3$ | CH$_3$ | N | O | |
| 2-CH$_3$ | CH$_3$ | CH$_3$ | N | O | |
| 3-Br | OCH$_3$ | OCH$_3$ | N | O | |
| 3-OCH$_3$ | OCH$_3$ | OCH$_3$ | CH | O | |
| 4-OCH$_3$ | OCH$_3$ | OCH$_3$ | CH | O | |
| 4-CH$_3$ | OCH$_3$ | OCH$_3$ | CH | O | |
| 5-Cl | OCH$_3$ | OCH$_3$ | CH | O | |
| 5-CH$_3$ | OCH$_3$ | OCH$_3$ | CH | O | |
| 6-Cl | OCH$_3$ | OCH$_3$ | N | O | |
| 6-CH$_3$ | OCH$_3$ | OCH$_3$ | N | O | |
| 6-OCH$_3$ | OCH$_3$ | OCH$_3$ | N | O | |

TABLE I-continued

| R₁ | X | Y | Z | W | m.p. (°C.) |
|---|---|---|---|---|---|
| 7-F | OCH₃ | OCH₃ | N | O | |
| 7-F | OCH₃ | OCH₃ | CH | O | |
| 7-Cl | OCH₃ | OCH₃ | CH | O | 208–215 |
| 7-Cl | CH₃ | OCH₃ | CH | O | 154–172 |
| 7-Cl | CH₃ | CH₃ | CH | O | 169–191(d) |
| 7-Cl | CH₃ | CH₃ | N | O | 161–166(d) |
| 7-Cl | CH₃ | OCH₃ | N | O | 132(d) |
| 7-Cl | OCH₃ | OCH₃ | N | O | 188(d) |
| 7-Br | OCH₃ | OCH₃ | N | O | |
| 7-OCH₃ | OCH₃ | OCH₃ | N | O | |
| 7-CH₃ | OCH₃ | OCH₃ | N | O | |
| 7-NO₂ | OCH₃ | OCH₃ | N | O | |
| 7-CO₂CH₃ | OCH₃ | OCH₃ | CH | O | |
| 7-CO₂(CH₂)₃CH₃ | OCH₃ | OCH₃ | CH | O | |
| 7-CO₂CH₂CHCH₂ | OCH₃ | OCH₃ | CH | O | |
| 7-CO₂CH₂CHCHCH₃ | OCH₃ | OCH₃ | CH | O | |
| 7-CO₂CH₂CH₂Cl | OCH₃ | OCH₃ | CH | O | |
| 7-CO₂CH₂CH₂OCH₃ | OCH₃ | OCH₃ | CH | O | |
| 7-SCH₃ | OCH₃ | OCH₃ | CH | O | |
| 7-SCH(CH₃)₂ | OCH₃ | OCH₃ | CH | O | |
| 7-SCH₂CH₂CH₂CH₃ | OCH₃ | OCH₃ | CH | O | |
| 7-S(O)CH₃ | OCH₃ | OCH₃ | CH | O | |
| 7-SO₂CH₃ | OCH₃ | OCH₃ | CH | O | |
| 7-SO₂CH₂CH₂CH₃ | OCH₃ | OCH₃ | CH | O | |
| 7-SO₂N(CH₃)₂ | OCH₃ | OCH₃ | CH | O | |
| 7-SO₂N(CH₂CH₃)(CH(CH₃)₂) | OCH₃ | OCH₃ | CH | O | |
| 7-SO₂N(CH₃)(CH₂CH₂CH₂CH₃) | OCH₃ | OCH₃ | CH | O | |
| 7-SO₂N(OCH₃)CH₃ | OCH₃ | OCH₃ | CH | O | |
| 7-OSO₂CH₃ | OCH₃ | OCH₃ | CH | O | |
| 7-OSO₂CH₂(CH₃)C₂H₅ | OCH₃ | OCH₃ | CH | O | |
| 7-OSO₂CF₃ | OCH₃ | OCH₃ | CH | S | |
| H | OCH₃ | OCH₃ | CH | S | |
| H | OCH₃ | OCH₃ | N | S | |
| 7-CH₃ | OCH₃ | OCH₃ | N | S | |
| 7-Cl | OCH₃ | OCH₃ | N | S | |

TABLE II

| R₁ | X | Y | Z | W |
|---|---|---|---|---|
| H | CH₃ | OCH₃ | CH | O |
| H | CH₂CH₂OCH₃ | OCH₃ | CH | O |
| H | OCH₃ | OCH₃ | CH | O |
| H | N(CH₃)₂ | OCH₃ | CH | O |
| H | CH₃ | CH₃ | CH | O |
| H | CH₃ | CH₃ | N | O |
| H | OCH₃ | CH₃ | N | O |
| H | OCH₃ | OCH₃ | N | O |
| H | OCH₃ | OCH₃ | N | S |
| H | OCH₃ | OCH₃ | CH | S |
| 2-CH₃ | OCH₃ | OCH₃ | N | O |
| 3-Br | OCH₃ | OCH₃ | N | O |
| 4-OCH₃ | OCH₃ | OCH₃ | N | O |
| 6-F | OCH₃ | OCH₃ | N | O |
| 6-Cl | OCH₃ | OCH₃ | N | O |
| 6-Cl | CH₃ | OCH₃ | N | O |
| 6-Cl | CH₃ | CH₃ | N | O |
| 6-Cl | CH₃ | CH₃ | CH | O |
| 6-Cl | CH₃ | OCH₃ | CH | O |
| 6-Cl | OCH₃ | OCH₃ | CH | O |
| 6-OCH₃ | OCH₃ | OCH₃ | CH | O |
| 6-NO₂ | OCH₃ | OCH₃ | CH | O |
| 6-CO₂CH₃ | OCH₃ | OCH₃ | CH | O |
| 6-SCH₃ | OCH₃ | OCH₃ | CH | O |
| 6-SO₂CH₃ | OCH₃ | OCH₃ | CH | O |
| 7-Cl | OCH₃ | OCH₃ | CH | O |
| 8-OCH₃ | OCH₃ | OCH₃ | CH | O |

TABLE III

| R₁ | X | Y | Z | m.p. (°C) |
|---|---|---|---|---|
| H | CH₃ | OCH₃ | CH | |
| H | CH₃ | CH₃ | CH | |
| H | OCH₃ | OCH₃ | CH | |
| H | CH₂CH₃ | CH₃ | CH | |
| H | CH₃ | OCH₃ | N | 205–208 |
| H | OCH₃ | OCH₃ | N | |
| H | CH₃ | CH₃ | N | |
| 2-F | OCH₃ | OCH₃ | CH | |
| 3-Br | OCH₃ | OCH₃ | CH | |
| 4-OCH₃ | OCH₃ | OCH₃ | CH | |
| 5-CH₃ | OCH₃ | CH₃ | N | |
| 6-CH₃ | OCH₃ | CH₃ | N | |
| 7-Cl | OCH₃ | CH₃ | CH | |
| 7-Br | OCH₃ | CH₃ | CH | |
| 7-NO₂ | OCH₃ | CH₃ | CH | |
| 7-OCH₃ | OCH₃ | CH₃ | CH | |
| 7-CO₂CH₃ | OCH₃ | CH₃ | CH | |
| 7-SO₂CH₃ | OCH₃ | CH₃ | CH | |
| 7-SO₂N(CH₃)₂ | OCH₃ | CH₃ | CH | |
| 7-SO₂N(OCH₃)CH₃ | OCH₃ | CH₃ | CH | |

TABLE IV

| R₁ | X | Y | Z |
|---|---|---|---|
| H | CH₃ | OCH₃ | CH |
| H | CH₃ | CH₃ | CH |
| H | OCH₃ | OCH₃ | CH |
| H | CH₂CH₃ | CH₃ | CH |
| H | CH₃ | OCH₃ | N |
| H | OCH₃ | OCH₃ | N |
| H | CH₃ | CH₃ | N |
| 2-F | OCH₃ | OCH₃ | CH |
| 3-Br | OCH₃ | CH₃ | N |
| 4-OCH₃ | OCH₃ | CH₃ | N |
| 6-Cl | OCH₃ | CH₃ | CH |
| 6-Br | OCH₃ | CH₃ | CH |
| 6-NO₂ | OCH₃ | CH₃ | CH |
| 6-OCH₃ | OCH₃ | CH₃ | CH |
| 6-CH₃ | OCH₃ | CH₃ | CH |
| 6-CO₂CH₃ | OCH₃ | CH₃ | CH |
| 6-SO₂CH₃ | OCH₃ | CH₃ | CH |
| 6-SO₂N(CH₃)₂ | OCH₃ | CH₃ | CH |
| 6-SO₂N(OCH₃)CH₃ | OCH₃ | CH₃ | CH |
| 7-Cl | OCH₃ | CH₃ | CH |
| 8-OCH₃ | OCH₃ | CH₃ | N |

TABLE V

| R₁ | X' | Y' | Z | m.p. (°C) |
|---|---|---|---|---|
| H | Cl | Cl | CH | 198–200 |
| H | Cl | Br | CH | |
| H | Br | Br | CH | |
| H | Br | Br | N | |
| H | Br | Cl | N | |
| H | Cl | Cl | N | 145–147 |
| 2-Cl | Cl | Cl | N | |
| 3-Br | Cl | Cl | N | |
| 4-OCH₃ | Cl | Cl | N | |
| 4-CH₃ | Cl | Cl | CH | |
| 5-Cl | Cl | Cl | CH | |
| 6-CH₃ | Cl | Cl | CH | |
| 7-F | Cl | Cl | CH | |
| 7-Cl | Cl | Cl | CH | |
| 7-Cl | Cl | Cl | N | |
| 7-NO₂ | Cl | Cl | N | |
| 7-CO₂CH₃ | Cl | Cl | N | |
| 7-CO₂CH₂CH₂CH₂CH₃ | Cl | Cl | N | |
| 7-CO₂CH₂CHCH₃ | Cl | Cl | N | |
| 7-CO₂CH₂CH₂Cl | Cl | Cl | N | |
| 7-CO₂CH₂CH₂OCH₃ | Cl | Cl | N | |
| 7-SCH₃ | Cl | Cl | CH |
| 7-SO₂CH(CH₃)C₂H₇ | Cl | Cl | CH |
| 7-SO₂N(CH₃)₂ | Cl | Cl | CH |
| 7-SO₂N(CH₃)t-C₄H₉ | Cl | Cl | CH |
| 7-SO₂N(OCH₃)CH₃ | Cl | Cl | CH |
| 7-OSO₂CH₃ | Cl | Cl | N |
| 7-OSO₂CH₂CH₂CH₃ | Cl | Cl | N |
| 7-OSO₂CH₂CH₂CH₂CH₃ | Cl | Cl | CH |

TABLE V-continued

[Structure: naphthalene ring system with N at position 1, R₁ at positions 2/3, SO₂NHCNH group with C=O at position 8, connected to a pyrimidine ring with substituents X', Y', Z]

| R₁ | X' | Y' | Z | m.p. (°C.) |
|---|---|---|---|---|
| 7-OSO₂CF₃ | Cl | Cl | CH | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE VI

| | Active Ingredient | Diluent(s) | Weight Percent* Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 11

Wettable Powder

| | |
|---|---|
| N—[(4,6-dimethoxypyrimidin-2-yl)aminocarbonyl]-8-quinolinesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 12

Wettable Powder

| | |
|---|---|
| N—[(4,6-dimethylpyrimidin-2-yl)aminocarbonyl]-8-quinolinesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 13

Granule

| | |
|---|---|
| Wettable Powder of Example 12 | 5% |
| attapulgite granules | 95% |

A slurry of wettable powder containing 25% solids is sprayed on the surface of attapulgite granules in a double-cone blender. The granules are dried and packaged.

EXAMPLE 14

Extruded Pellet

| | |
|---|---|
| N—[(4,6-dimethoxy-1,3,5-triazin-2-yl)aminocarbonyl]-8-quinolinesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 15

Oil Suspension

| | |
|---|---|
| 7-Chloro-N—[(4,6-dimethoxypyrimidin-2-yl)aminocarbonyl]-8-quinolinesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 16

Wettable Powder

| | |
|---|---|
| N—[(4-methoxy-6-methylpyrimidin-2-yl)aminocarbonyl]-8-quinolinesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 17

Low Strength Granule

| | |
|---|---|
| 7-Chloro-N—[(4,6-dimethoxy-1,3,5-triazin-2-yl)aminocarbonyl]-8-quinolinesulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and than the granules are packaged.

EXAMPLE 18

Aqueous Suspension

| | |
|---|---|
| 7-Chloro-N—[(4-methoxy-6-methylpyrimidin-2-yl)aminocarbonyl]-8-quinolinesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 19

Solution

| | |
|---|---|
| 7-Chloro-N—[(4-dimethyl-1,3,5-triazin-2-yl)aminocarbonyl]-8-quinolinesulfonamide, sodium salt | 5% |
| water | 95% |

The salt is added directly to the water with stirring to produce the solution, which may then be packaged for use.

EXAMPLE 20

Low Strength Granule

| | |
|---|---|
| 7-Chloro-N—[(4,6-dimethylpyrimidin-2-yl)aminocarbonyl]-8-quinolinesulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 21

Granule

| | |
|---|---|
| N—[(4-methoxy-6-methyl-1,3,5-triazin-2-yl)aminocarbonyl]-8-quinolinesulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 22

High Strength Concentrate

| | |
|---|---|
| N—[(4,6-dimethoxy-1,3,5-triazin-2-yl)amino-carbonyl]-8-quinolinesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 23

Wettable Powder

| | |
|---|---|
| N—[(4,6-dimethyl-1,3,5-triazin-2-yl)aminocarbonyl]-8-quinolinesulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 24

Wettable Powder

| | |
|---|---|
| N—(4-methoxy-6-methyl-1,3,5-triazin-2-yl)-N'—(8-quinolinylsulfonyl)carbamimidothioic acid, methyl ester | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 25

Oil Suspension

| | |
|---|---|
| 7-Chloro-N—[(4-methoxy-6-methyl-1,3,5-triazin-2-yl)-aminocarbonyl]-8-quinolinesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

Utility

The compounds of the present invention are active herbicides. They have utility for broadspectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, certain compounds of this invention may be useful for the selective pre- or post-emergence weed control in crops such as wheat, soybeans and rice.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.125 to 10 kg/ha, the lower rates being suggested for use on lighter soils and/or those having a low organic matter content, for selective weed control or for situations where only short-term persistence is required.

The compounds of the invention may be used in combination with any other commercial herbicide examples of which are those of the triazine, triazole, uracil, urea, amide, diphenylether, carbamate and bipyridylium types.

The herbicidal properties of the subject compounds were discovered in a number of greenhouse tests. The test procedures and results follow.

Test A

Seeds of crabgrass (*Digitaria* spp.), barnyardgrass (*Echinochloa crusgalli*), wild oats (*Avena fatua*), Cassia *tora*, morningglory (*Ipomoea* spp.), cocklebur (*Xanthium* spp.), sorghum, corn, soybean, rice, wheat as well as nutsedge tubers were planted in a growth medium and treated pre-emergence with the chemicals dissolved in a non-phytotoxic solvent. At the same time, cotton having five leaves (including cotyledonary ones), bush beans with the third trifoliate leaf expanding, crabgrass, barnyardgrass and wild oats with two leaves, cassia with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three-five leaves were sprayed. Treated plants and controls were maintained in a greenhouse for sixteen days, whereupon all species were compared to controls and visually rated for response to treatment. The ratings are based on a numerical scale extending from 0=no injury to 10=complete kill. The accompanying descriptive symbols have the following meanings: G=growth retardation; C=chlorosis/necrosis; D=defoliation; 6Y=abscised buds or flowers; U=unusual pigmentation; E=emergence inhibition; and H=formative effects. The ratings for the compounds tested by this procedure are presented in Table A. It will be seen that certain of the compounds tested have utility for selective post-emergence weed control in wheat.

TABLE A

| | | kg/ha | BUSH-BEAN | COT-TON | MORN-ING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|---|
| ![structure 1] | | 0.4 | 9D,9G,6Y | 0 | 6G | 8H | 2C,8G | 0 | — | 2C,6H | 0 | 1C | 1C,9G | 2C,9G | 3C,9G | 2C,9G |
| ![structure 2] | | 2 | 0 | 0 | 0 | 0 | 0 | 0 | 0 | 0 | 0 | 0 | 0 | 0 | 0 | 0 |
| ![structure 3] | | 2 | 6C,9G,6Y | 7C,9G | 9C | 9C | 9C | 4C,9G | 5C,9G | 6C,9G | 2C,9G | 2C,9G | 5C,9G | 9C | 5C,9G | 1C,9G |
| ![structure 4] | | 0.4 | 3C,4G,6Y | 2C | 2C | 1C,4G | 2G | 0 | 0 | 2C,3G | 0 | 0 | 1C,7G | 1C,1H | 1C | 1C,5G |

TABLE A-continued

| Structure | | | | | | | | | | | | | |
|---|---|---|---|---|---|---|---|---|---|---|---|---|---|
| 8-quinolinyl-SO₂-NH-C(O)-NH-pyrimidine(2-OCH₃, 6-OCH₃) | 0.4 | 9C | 9C | 10C | 9C | 9C | 3C,7G | 8C | 6C,9H | 6C,8G | 1C,7G | 8U,9C | 9C | 6C,8G | 9C |
| 8-quinolinyl-SO₂-NH-C(O)-NH-pyrimidine(2-OCH₃, 6-CH₃) | 0.05 | 9C | 5C,8G | 3C | 10C | 4C,8G | 0 | 3G | 2C,9H | 2C,3G | 2C,9G | 7U,9C | 9C | 6C,9G | 3U,9H |
| 8-quinolinyl-SO₂-NH-C(O)-NH-pyrimidine(2-CH₃, 6-CH₃) | 0.05 | 5C,9G,6Y | 1C,2H | 9H | 2C,5H | 0 | 0 | 1H | 0 | 2C,9H | 4H | 2C,7G | 3C,8H |
| 8-quinolinyl-SO₂-NH-C(O)-NH-pyrimidine(2-OCH₃, 6-OCH₃) | 0.05 | 9C | 5C,9H | 2C,7G | 3C,9G | 5C,9G | 2G | 1C | 2C,8H | 3C,9G | 2C,8G | 10C | 2C,9G | 4C,9G | 2C,9H |

TABLE A-continued

| Structure | | | | | | | | | | | |
|---|---|---|---|---|---|---|---|---|---|---|---|
| 8-quinolinyl-SO₂-NH-C(O)-NH-(4,6-dimethyl-triazin-2-yl) | 0.05 | 3C,6H,6Y | 0 | 3H | 2C,8H | 1C | 0 | 0 | 0 | 1C,3H | 0 | 1C,7G | 1C,3H |
| 7-Cl-8-quinolinyl-SO₂-NH-C(O)-NH-(4,6-dimethyl-triazin-2-yl) | 0.4 | 9C | 0 | 0 | 2G | 0 | 0 | 0 | 0 | 2H | 0 | 2H | 6H |
| 7-Cl-8-quinolinyl-SO₂-NH-C(O)-NH-(4-methyl-6-methoxy-triazin-2-yl) | 0.4 | 9C | 3C,9G | 3C,9G | 10C | 4C,8G | 3C,8G | 0 | 5C,9H | 0 | 6U,9C | 3C,9G | 5C,9G | 4U,9C |
| 7-Cl-8-quinolinyl-SO₂-NH-C(O)-NH-(4,6-dimethoxy-triazin-2-yl) | 0.4 | 9C | 5C,9G | 4C,9G | 9C | 3C,8G | 3C,8G | 0 | 2C,8H | 1C | 1C | 4U,9H | 5C,9G | 5C | 2C |

TABLE A-continued

| Structure | kg/ha | | | | | | | | | | | | | |
|---|---|---|---|---|---|---|---|---|---|---|---|---|---|---|
| Cl-quinolin-8-yl-SO₂—NH—C(O)—NH-(4,6-dimethylpyrimidin-2-yl) | 0.4 | 6F | 2C,5H | 0 | 1H | 2C | 0 | 0 | 0 | 0 | 2C,9H | 1C,5H | 9G | 2C,9H |
| Cl-quinolin-8-yl-SO₂—NH—C(O)—NH-(4-methyl-6-methoxypyrimidin-2-yl) | 0.4 | 8C | 4C,9G | 2C | 4C,8H | 3C,9G | 2C,8G | 3C,9H | 2C,2G | 0 | 2U,9G | 3C,9G | 3C,9G | 2U,9G |
| Cl-quinolin-8-yl-SO₂—NH—C(O)—NH-(4,6-dimethoxypyrimidin-2-yl) | 0.4 | 6C,9G | 2C | 4C,9H | 5C,9G | 4C,9G | 1C,3G | 5C,9H | 2C,6G | 2C,5G | 5U,9C | 3C,9H | 2C,9G | 3C,9G |

PRE-EMERGENCE

| Structure | kg/ha | MORNING-GLORY | COCKLE-BUR | CASSIA | NUTSEDGE | CRABGRASS | BARN-YARD-GRASS | WILD OATS | WHEAT | CORN | SOYBEAN | RICE | SORGHUM |
|---|---|---|---|---|---|---|---|---|---|---|---|---|---|
| quinolin-8-yl-SO₂—N=C(SCH₃)—NH-(4-methoxy-6-methylpyrimidin-2-yl) | 0.4 | 1C,7H | 0 | 1C,5G | 0 | 1C,3G | 3G | 7G | 1C,5G | 1C,2H | 9H | 1C,9G | |

TABLE A-continued

| Structure | Rate | | | | | | | | | | | | | |
|---|---|---|---|---|---|---|---|---|---|---|---|---|---|---|
| Quinoline-8-SO₂—NH—C(O)—NH-(4,6-dichloro-1,3,5-triazin-2-yl) | 2 | 0 | 5G | 0 | 0 | 10E | 2G | 0 | 0 | 0 | 2G | 0 | 5G | 1C,3G |
| Quinoline-8-SO₂—NH—C(O)—NH-(4,6-dimethoxy-1,3,5-triazin-2-yl) | 2 | 9H | 9H | 9G | 10E | 3C,9G | 9H | 3C,9H | 1C,9H | 10E | 9H | 10E | 6C,9H |
| Quinoline-8-SO₂—NH—C(O)—NH-(4,6-dichloropyrimidin-2-yl) | 0.4 | 1C,5G | 5G | 1C,5G | 0 | 2G | 1C | 0 | 0 | 1C,4G | 0 | 0 | 2G |
| Quinoline-8-SO₂—NH—C(O)—NH-(4,6-dimethoxypyrimidin-2-yl) | 0.4 | 9G | 9H | 9G | 10E | 3C,9H | 9H | 3C,9H | 9H | 9H | 9H | 10E | 9H |

TABLE A-continued

| Structure | Rate | 6G | 9H | 8H | | | 2C,9H | 2C,6G | 3C,9H | 2C,9G | 3C,6H | 10E | 9H |
|---|---|---|---|---|---|---|---|---|---|---|---|---|---|
| Quinoline-8-SO₂—NH—C(O)—NH— triazine (OCH₃, OCH₃) | 0.05 | 6G | 9H | 8H | 0 | 0 | 2C,9H | 2C,6G | 3C,9H | 2C,9G | 3C,6H | 10E | 9H |
| Quinoline-8-SO₂—NH—C(O)—NH— pyrimidine (CH₃, CH₃) | 0.05 | 0 | 0 | 0 | 0 | 0 | 0 | 0 | 0 | 0 | 0 | 0 | 0 |
| Quinoline-8-SO₂—NH—C(O)—NH— pyrimidine (OCH₃, OCH₃) | 0.05 | 2C,8G | 9H | 4C,5G | 4G | 3C,4G | 5C,9H | 6C,9G | 2C,9H | 1C,9G | 2C,8H | 10E | 1C,9H |
| Quinoline-8-SO₂—NH—C(O)—NH— triazine (CH₃, CH₃) | 0.05 | 0 | 0 | 0 | 0 | 0 | 0 | 0 | 0 | 0 | 0 | 0 | 0 |

TABLE A-continued

| Structure | | | | | | | | | | | | | |
|---|---|---|---|---|---|---|---|---|---|---|---|---|---|
| Cl-quinoline-SO₂-NH-C(=O)-NH-[pyrimidine-2,6-(CH₃)₂] | 0.4 | 0 | — | 0 | 0 | 0 | 0 | 0 | 0 | 0 | 0 | 0 | 0 |
| Cl-quinoline-SO₂-NH-C(=O)-NH-[pyrimidine-2-CH₃,6-OCH₃] | 0.4 | 9G | 9H | 4C,9G | 3G | 0 | 3C,9H | 2C,6G | 1C,5G | 9H | 2C,7H | 10E | 2C,9G |
| Cl-quinoline-SO₂-NH-C(=O)-NH-[pyrimidine-2,6-(OCH₃)₂] | 0.4 | 9G | 9H | 2C,7G | 1C,4G | 2C | 3C,8G | 3C,7G | 2C,7G | 3C,9G | 2C,6H | 10E | 2C,9G |
| Cl-quinoline-SO₂-NH-C(=O)-NH-[pyridine-2,6-(CH₃)₂] | 0.4 | 0 | 8H | 1C | 0 | 0 | 0 | 0 | 0 | 2C,6G | 2C | 3C,7G | 2C |

TABLE A-continued

| Structure | | | | | | | | | | | |
|---|---|---|---|---|---|---|---|---|---|---|---|
| 2-Cl-quinoline-SO2NHC(O)NH-(4-CH3-6-OCH3-pyrimidin-2-yl) | 0.4 | 9G | 9H | 2C,9G | 3G | 2C | 2C,9H | 3C,9H | 2C,7G | 2C,9G | 3C,6H | 3C,9H | 9G |
| 2-Cl-quinoline-SO2NHC(O)NH-(4-OCH3-6-OCH3-pyrimidin-2-yl) | 0.4 | 8G | 9H | 2C,8G | 10E | 2C,5G | 2C,9H | 3C,9H | 3C,8G | 3C,9G | 2C,8H | 10E | 2C,9H |

Test B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*) wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pennsylvanicum*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter paper cup was also filled with prepared soil and planted with rice and wheat. Another 12.5 cm cup was planted with sugarbeets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B. Note that certain compounds are useful as pre-emergence treatments for weed control in crops such as soybeans and wheat.

TABLE B
PRE-EMERGENCE ON FALLSINGTON SILT LOAM

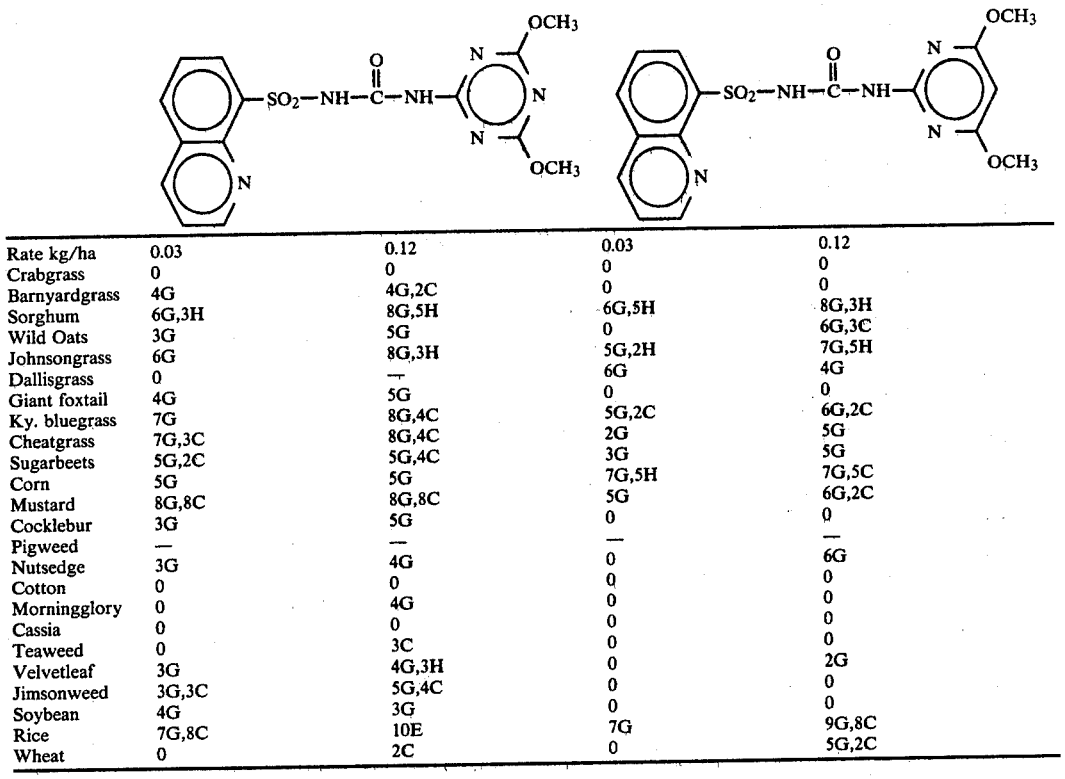

| | | | | |
|---|---|---|---|---|
| Rate kg/ha | 0.03 | 0.12 | 0.03 | 0.12 |
| Crabgrass | 0 | 0 | 0 | 0 |
| Barnyardgrass | 4G | 4G,2C | 0 | 0 |
| Sorghum | 6G,3H | 8G,5H | 6G,5H | 8G,3H |
| Wild Oats | 3G | 5G | 0 | 6G,3C |
| Johnsongrass | 6G | 8G,3H | 5G,2H | 7G,5H |
| Dallisgrass | 0 | — | 6G | 4G |
| Giant foxtail | 4G | 5G | 0 | 0 |
| Ky. bluegrass | 7G | 8G,4C | 5G,2C | 6G,2C |
| Cheatgrass | 7G,3C | 8G,4C | 2G | 5G |
| Sugarbeets | 5G,2C | 5G,4C | 3G | 5G |
| Corn | 5G | 5G | 7G,5H | 7G,5C |
| Mustard | 8G,8C | 8G,8C | 5G | 6G,2C |
| Cocklebur | 3G | 5G | 0 | 0 |
| Pigweed | — | — | — | — |
| Nutsedge | 3G | 4G | 0 | 6G |
| Cotton | 0 | 0 | 0 | 0 |
| Morningglory | 0 | 4G | 0 | 0 |
| Cassia | 0 | 0 | 0 | 0 |
| Teaweed | 0 | 3C | 0 | 0 |
| Velvetleaf | 3G | 4G,3H | 0 | 2G |
| Jimsonweed | 3G,3C | 5G,4C | 0 | 0 |
| Soybean | 4G | 3G | 0 | 0 |
| Rice | 7G,8C | 10E | 7G | 9G,8C |
| Wheat | 0 | 2C | 0 | 5G,2C |

Test C

In Test C, plastic pots filled with Fallsington silt loam were planted to soybeans, cotton, alfalfa, corn, rice, wheat, sorghum, velvetleaf (*Abutilon theophrasti*), sesbania (*Sesbania exaltata*), cassia (*Cassia tora*), morningglory (*Ipomoea* spp.), jimsonweed (*Datura stramonium*), cocklebur (*Xanthium pennsylvanicum*), crabgrass (*Digitaria* spp.), nutsedge (*Cyperus rotundus*), barnyardgrass (*Echinochloa crusgalli*), giant foxtail (*Setaria faberii*) and wild oats (*Avena fatua*). Eighteen days after planting, the young plants and the soil around them were sprayed overall with the test chemical dissolved in a nonphytotoxic solvent. Fourteen days after treatment, all species were compared to untreated controls and visually rated for response to treatment utilizing the rating system described previously for Test A. The data for the compounds tested by this procedure are presented in Table C.

TABLE C
OVER-THE-TOP SOIL/FOLIAGE TREATMENT

| Structure | Rate kg/ha | Soy-beans | Vel-vet-leaf | Ses-bania | Cassia | Cotton | Morn-ing-glory | Al-falfa | Jim-son-weed | Cockle-bur | Corn | Crab-grass | Rice | Nut-sedge | Barn-yard-grass | Wheat | Giant Foxtail | Wild Oats | Sor-ghum |
|---|---|---|---|---|---|---|---|---|---|---|---|---|---|---|---|---|---|---|---|
| 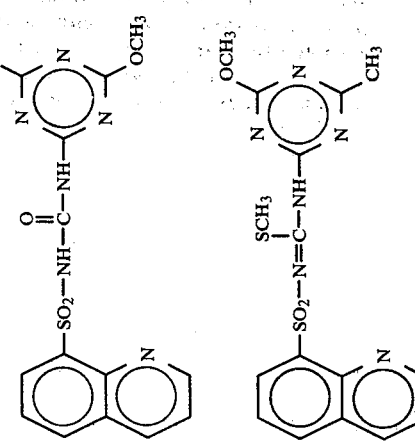 | 0.015 | 9G, 3C | 4G, 2C | 7G, 3C | 4G, 3C | 0 | 4G, 2C | 1C | 8G, 4C | 10G, 7C | 8G, 2C | 8G, 2C | 9G, 3C | 0 | 8G, 3C | 0 | 7G, 2C | 9G, 6C | 7G, 3C |
| | 0.06 | 10G, 6C | 10G, 7C | 10G, 7C | 9G, 7C | 5G, 3C | 7G, 3C | 3C | 7G, 3C | 10G, 6C | 9C | 6G, 3C | 8G, 3C | 2C | 7G, 2C | 6G, 3C | 7G, 2C | 8G, 3C | 8G, 3C |
| | 0.25 | 9G, 7C | 9C | 10G, 8C | 10G, 7C | 10G, 8C | 10G, 7C | 8G, 6C | 3C, 0 | 10G, 7C | 10C | 0 | 9G, 7C | 7G | 3G, 1C | 7G | 2C | 3C, 1G | 9G, 6C |
| 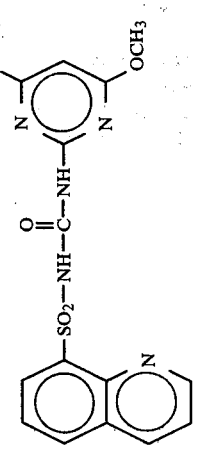 | 0.06 | 8G, 2C | 5G | 7G, 1C | 4G | 2G | 6G | 6G, 3C | 8G, 1C | 3G | 10G, 6H | 0 | 8G, 2C | 2G | 0 | 0 | 5G, 2C | 0 | 10G, 2C |
| | 0.25 | 8G, 3C | 6G, 3H | 8G, 3C | 5G, 2C | 3G | 8G | 9G, 5C | 7G, 3C | — | 5G, 2H | 10G, 2U | 2G | 10G, 4C | 4G | 2G | 0 | 4G | 0 | 10G, 2C |
| (third structure) | 0.008 | 9G, 4C | 7G, 3C | 7G, 3C | 1C | 0 | 6G, 1C | 3C | 3G, 2C | 5G, 5H | 10G, 9C | 0 | 6G, 1C | 6G, 3C | 7G, 3C | 3G | 0 | 3C | 10C |
| | 0.03 | 10G, 7C | 9C, 3G | 8G, 3C | 5G, 1C | 5G, 2C | 9G, 4C | 7C | 0 | 9G, 5H | 10C | 2G | 9G, 2C | 7G, 3C | 8G, 4C | 3G | 1G | 7G, 3C | 10C |
| | 0.06 | 7C | 10C | 4G, 3C | 10G, 8C | 7C | 8G, 3C | 10G, 7C | 6G, 2C | 10G, 7C | 10C | 1C | 9G, 4C | 9G, 5C | 8G, 3C | 7G, 2C | 6G, 3C | 9G, 6C | 10C |
| | 0.25 | 10G, 9C | 10C | 10G, 8C | 10G, 8C | 9G, 10C | 10G, 8C | 10G, 8C | 9G, 9C | 10G, 8C | 10C | 6G, 2C | 10G, 7C | 10G, 7C | 8G, 6C | 8G, 3C | 7G, 3C | 10C | 10C |

What is claimed is:
1. A compound selected from

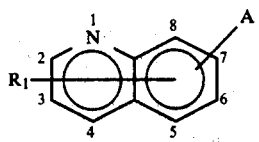

wherein
A is

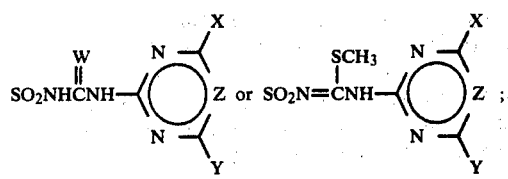

$R_1$ is H, F, Cl, Br, $OCH_3$, $CH_3$, $NO_2$, $CO_2R_2$, $S(O)_nR_3$, $SO_2NR_4R_5$, $SO_2N(OCH_3)CH_3$ or $OSO_2R_6$;
$R_2$ is $C_1$-$C_4$ alkyl, $C_3$-$C_4$ alkenyl, $CH_2CH_2Cl$ or $CH_2CH_2OCH_3$;
$R_3$ is $C_1$-$C_4$ alkyl;
$R_4$ and $R_5$ are independently $C_1$-$C_4$ alkyl;
$R_6$ is $C_1$-$C_4$ alkyl or $CF_3$;
n is 0, 1 or 2;
X is $C_1$-$C_2$ alkyl, $C_1$-$C_2$ alkyl substituted with $OCH_3$, $CF_3$, $C_1$-$C_3$ alkoxy, $N(CH_3)_2$, $NHCH_3$, $NH_2$, or $SCH_3$;
Y is $CH_3$, $OCH_3$ or Cl;
Z is N; and
W is O or S;
and their agricultural salts; provided that
(1) A is in the 5 or 8 position of the quinoline ring;
(2) when $R_1$ is $NO_2$, $CO_2R_2$, $S(O)_nR_3$, $SO_2NR_4R_5$, $SO_2N(OCH_3)CH_3$ or $OSO_2R_6$, then $R_1$ is at the 6-position when A is at the 5-position, and $R_1$ is at the 7-position when A is at the 8-position of the quinoline ring; 7-position of the quinoline ring;
(3) the total number of carbon atoms of $R_4$ and $R_5$ is less than or equal to 5; and
(4) when Y is Cl, then Z is CH and X is $NH_2$, $NHCH_3$, $N(CH_3)_2$ or $OCH_3$.
2. A compound of claim 1 in which A is in the 8-position of the quinoline ring; $R_1$ is H, Cl, Br, $OCH_3$, $CO_2CH_3$ or $NO_2$; and W is O.
3. A compound of claim 2 where $R_1$ is in the 7-position of the quinoline ring.
4. A compound of claim 3 where A is

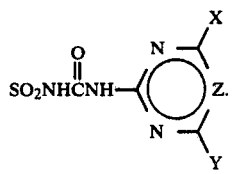

5. A compound of claim 4 where X is $CH_3$ or $OCH_3$.
6. A compound of claim 5 where $R_1$ is H, Cl Br or $OCH_3$.

7. The compound of claim 1, N-[(4,6-dimethoxy-1,3,5-triazin-2-yl)aminocarbonyl]-8-quinolinesulfonamide.
8. The compound of claim 1, N-[(4,6-dimethyl-1,3,5-triazin-2-yl)aminocarbonyl]-8-quinolinesulfonamide.
9. The compound of claim 1, N-[(4-methoxy-6-methyl-1,3,5-triazin-2-yl)aminocarbonyl]-8-quinolinesulfonamide.
10. The compound of claim 1, N-[(4-methoxy-6-methyl-1,3,5-triazin-2-yl)-N']-(8-quinolinylsulfonyl)carbamimidothioic acid, methyl ester.
11. The compound of claim 1, 7-Chloro-N-[(4,6-dimethoxy-1,3,5-triazin-2-yl)aminocarbonyl]-8-quinolinesulfonamide.
12. The compound of claim 1, 7-Chloro-N-[(4,6-dimethyl-1,3,5-triazin-2-yl)aminocarbonyl]-8-quinolinesulfonamide.
13. The compound of claim 1, 7-Chloro-N-[(4-methoxy-6-methyl-1,3,5-triazin-2-yl)aminocarbonyl]-8-quinolinesulfonamide.
14. A compound selected from

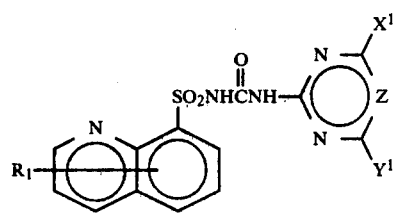

$R_1$ is H, F, Cl, Br, $OCH_3$, $CH_3$, $NO_2$, $CO_2R_2$, $S(O)_nR_3$, $SO_2NR_4R_5$, $SO_2N(OCH_3)CH_3$ or $OSO_2R_6$;
$R_2$ is $C_1$-$C_4$ alkyl, $C_3$-$C_4$ alkenyl, $CH_2CH_2Cl$ or $CH_2CH_2OCH_3$;
$R_3$ is $C_1$-$C_4$ alkyl;
$R_4$ and $R_5$ are independently $C_1$-$C_4$ alkyl;
$R_6$ is $C_1$-$C_4$ alkyl or $CF_3$;
n is 0 or 2;
$X^1$ and $Y^1$ are independently Cl or Br; and
Z is N;
provided that
(1) when $R_1$ is $NO_2$, $CO_2R_2$, $S(O)_nR_3$, $SO_2NR_4R_5$, $SO_2N(OCH_3)CH_3$ or $OSO_2R_6$, the $R_1$ is in the 7-position of the quinoline ring; and
(2) the total number of carbon atoms of $R_4$ and $R_5$ is less than or equal to 5.
15. The compound of claim 14, N-[(4,6-dichloro-1,3,5-triazin-2-yl)aminocarbonyl]-8-quinolinesulfonamide.
16. A composition suitable for controlling the growth of undesired vegetation which comprises an effective amount of a compound of claim 1 and at least one of the following: surfactant, solid or liquid diluent.
17. A composition suitable for controlling the growth of undesired vegetation which comprises an effective amount of a compound of claim 2 and at least one of the following: surfactant, solid or liquid diluent.
18. A composition suitable for controlling the growth of undesired vegetation which comprises an effective amount of a compound of claim 3 and at least one of the following: surfactant, solid or liquid diluent.
19. A composition suitable for controlling the growth of undesired vegetation which comprises an effective amount of a compound of claim 4 and at least one of the following: surfactant, solid or liquid diluent.

20. A composition suitable for controlling the growth of undesired vegetation which comprises an effective amount of a compound of claim 5 and at least one of the following: surfactant, solid or liquid diluent.

21. A composition suitable for controlling the growth of undesired vegetation which comprises an effective amount of a compound of claim 6 and at least one of the following: surfactant, solid or liquid diluent.

22. A composition suitable for controlling the growth of undesired vegetation which comprises an effective amount of the compound of claim 7 and at least one of the following: surfactant, solid or liquid diluent.

23. A method for controlling the growth of undesired vegetation which comprises applying to the locus to be protected an effective amount of a compound of claim 1.

24. A method for controlling the growth of undesired vegetation which comprises applying to the locus to be protected an effective amount of a compound of claim 2.

25. A method for controlling the growth of undesired vegetation which comprises applying to the locus to be protected an effective amount of a compound of claim 3.

26. A method for controlling the growth of undesired vegetation which comprises applying to the locus to be protected an effective amount of a compound of claim 4.

27. A method for controlling the growth of undesired vegetation which comprises applying to the locus to be protected an effective amount of a compound of claim 5.

28. A method for controlling the growth of undesired vegetation which comprises applying to the locus to be protected an effective amount of a compound of claim 6.

29. A method for controlling the growth of undesired vegetation which comprises applying to the locus to be protected an effective amount of the compound of claim 7.

* * * * *